(12) United States Patent
Kaiga et al.

(10) Patent No.: US 8,802,007 B2
(45) Date of Patent: Aug. 12, 2014

(54) ULTRAVIOLET IRRADIATION SYSTEM AND WATER QUALITY MONITORING INSTRUMENT

(75) Inventors: Nobuyoshi Kaiga, Tokyo (JP); Soichiro Nakano, Tokyo (JP); Akinori Hatano, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/039,053

(22) Filed: Feb. 28, 2008

(65) Prior Publication Data

US 2008/0240997 A1    Oct. 2, 2008

(30) Foreign Application Priority Data

Mar. 1, 2007   (JP) .................................. 2007-051975

(51) Int. Cl.
*G01N 21/00* (2006.01)
*G01N 31/00* (2006.01)
*G01N 33/00* (2006.01)
*G01N 21/64* (2006.01)
*G01N 21/66* (2006.01)

(52) U.S. Cl.
USPC ......................................... 422/62; 422/82.08

(58) Field of Classification Search
CPC .... C02F 1/008; C02F 1/325; C02F 2201/326; C02F 2209/001; C02F 2209/11; G01N 21/64
USPC .................................................. 422/62, 80.8
See application file for complete search history.

(56) References Cited

U.S. PATENT DOCUMENTS

| 4,255,383 | A | 3/1981 | Schenck |
| 4,317,041 | A | 2/1982 | Schenck |
| 6,921,476 | B2 * | 7/2005 | Abe et al. ..................... 210/96.1 |
| 7,091,495 | B2 * | 8/2006 | Panico et al. ............. 250/432 R |
| 7,474,400 | B2 * | 1/2009 | Tartakovsky et al. ......... 356/317 |

FOREIGN PATENT DOCUMENTS

| DE | 27 35 550 A1 | 2/1979 |
| DE | 37 40 005 A1 | 6/1989 |
| DE | 195 30 086 A1 | 2/1997 |
| JP | 2003-90797 | 3/2003 |
| JP | 2003-260474 | 9/2003 |
| JP | 2004-243265 | 9/2004 |
| WO | WO 2006010252 A1 * | 2/2006 |

OTHER PUBLICATIONS

Takahashi et al., "Fluorescence Excitation Spectrometric Analysis and Evaluation of Fulvic-like Organic Matter in River Water," Journal of Japan Society on Water Environment (2003), 26:153-158.

(Continued)

*Primary Examiner* — Bobby Ramdhanie
*Assistant Examiner* — Bryan Kilpatrick
(74) *Attorney, Agent, or Firm* — Finnegan, Henderson, Farabow, Garrett & Dunner, L.L.P.

(57) ABSTRACT

A part of pre-treated water flowing into an ultraviolet irradiation tank is guided to a fluorometer. The fluorometer scans an excitation spectrum peak wavelength of the pre-treated water at a fluorescence wavelength fixed to 425 nm to obtain an excitation spectrum, and continuously measures an excitation peak wavelength thereof. Based on the analysis result obtained by the fluorometer, an ultraviolet irradiation device calculates an ultraviolet irradiation level target value for optimizing an ultraviolet irradiation level, and thus controls the irradiation level of ultraviolet rays emitted therefrom.

4 Claims, 7 Drawing Sheets

(56) References Cited

OTHER PUBLICATIONS

Official Action issued by the German Patent Office on Jul. 2, 2009, for German Patent Application No. 10 2008 012 254.8, and English-language translation thereof.
Official Action issued by the Canadian Patent Office on Jun. 15, 2011, for Canadian Patent Application No. 2,619,753.
Notification of a Preliminary Search Report Without Compulsory Reply from the French Patent Office mailed Apr. 8, 2011, for French Application No. 0851313, with English language translation thereof.
Second Office Action issued by the Chinese Patent Office on Dec. 13, 2011, for Chinese Patent Application No. 200810082285.2, and English-language translation thereof.

* cited by examiner

ULTRAVIOLET IRRADIATION SYSTEM AND WATER QUALITY MONITORING INSTRUMENT

CROSS REFERENCE TO RELATED APPLICATION

This application is based upon and claims the benefit of priority from Japanese Patent Application No. 2007-051975 filed on Mar. 1, 2007, the entire contents of which are incorporated herein by reference.

BACKGROUND OF THE INVENTION

1. Field of the Invention

The present invention relates to an ultraviolet irradiation system and a water quality monitoring instrument used in water treatment facilities for industrial water, for water purification processes putting great importance on securing water quality in terms of hygiene, and for the like. More particularly, the present invention relates to an ultraviolet irradiation system and a water quality monitoring instrument for optimizing an ultraviolet irradiation level by controlling the ultraviolet irradiation level while detecting water quality of water to be treated by using a fluorescence analysis to optimize the ultraviolet irradiation level.

2. Background Art

In facilities using river surface water as raw water, such as water treatment facilities, it is important to know beforehand a proportion of sewage mixed in river raw water for controlling treatment processes. Particularly, many water purification plants near a large city use the river surface water as the raw water. Thus, ammoniac nitrogen resulting from the sewage or chlorine-resistant pathogenic microorganisms contained in drainage from livestock farms located in an upstream region of a river cause a problem in the control of chlorination.

Particularly, in the treatment of the ammoniac nitrogen, it is required to install a chlorine demand meter which calculates a required amount of chlorine based on a residual chlorine amount after a sample is directly added with chlorine. Moreover, in the control by the residual chlorine and the treatment of chlorine-resistant pathogenic microorganisms, it is required to set the turbidity (specified by the Japanese Industrial Standards) of the treated water to 0.1 or less by controlling the accuracy in filtration (see Japanese Patent Application Publication Nos. 2003-260474 and 2003-90798).

SUMMARY OF THE INVENTION

Meanwhile, in such water treatment facilities, water to be treated is disinfected by, for example, a chlorination disinfection treatment, which is the most commonly used water disinfection treatment, and an ozonation treatment, which has been widely expanded in terms of the construction of the facility. However, all the water treatment methods have a problem of by-products. Accordingly, there is a trend to reduce the amount of such disinfectants to be injected.

Moreover, in recent years, along with the advancement in ultraviolet application technologies, ultraviolet disinfection has attracted attention as an alternative disinfection method against the problem caused by the chlorine-resistant pathogenic microorganisms such as cryptosporidium. The ultraviolet disinfection has characteristics such as generating no by-products. Moreover, time required for treatment by the ultraviolet disinfection is short. Additionally, it has been revealed in Japan that ultraviolet irradiation is significantly effective in the suppression of infectivity of cryptosporidium and the like. Furthermore, in the United States, the ultraviolet disinfection is said to be cost-effective for the inactivation of giardia lamblia and cryptosporidium.

However, in the water treatment method for disinfecting water to be treated by use of ultraviolet rays, the water to be treated is continuously irradiated with the ultraviolet rays at a constant intensity. Accordingly, an irradiation level becomes excessive or falls short when the properties or conditions of the water to be treated are changed. This brings about problems that reliability of the safety of the treated water is impaired and that excessive irradiation causes unnecessary energy consumption. Note that conventional examples of a water treatment system using a fluorometer are described in Japanese Patent Application Publication Nos. 2003-260474 and 2003-90797.

In consideration of the foregoing circumstances, it is an object of the present invention to provide an ultraviolet irradiation system capable of securing an optimum irradiation level even if the properties or conditions of water to be treated is changed and also capable of achieving reliability of the safety of the water treated by ultraviolet irradiation as well as energy saving.

In order to achieve the foregoing object, a first aspect of the present invention provides an ultraviolet irradiation system for disinfecting water by use of ultraviolet rays, the system including: a fluorometer disposed in at least one point in a process before a disinfection process, the fluorometer continuously measuring an excitation spectrum peak wavelength and/or a fluorescence spectrum peak wavelength; and an ultraviolet irradiation level control device that controls an ultraviolet irradiation level according to at least one of the excitation spectrum peak wavelength and the fluorescence spectrum peak wavelength obtained by the fluorometer.

In the ultraviolet irradiation system according to the first aspect, the ultraviolet irradiation level control device may control the ultraviolet irradiation level based on a proportional function, a step function or a predetermined function depending on the excitation spectrum peak wavelength and/or the fluorescence spectrum peak wavelength.

In the ultraviolet irradiation system according to the first aspect, the fluorometer may further continuously measures a fluorescence intensity; and the ultraviolet irradiation level control device may controls the ultraviolet irradiation level according to a water quality matrix representing a correlation between the fluorescence intensity and any one of the excitation spectrum peak wavelength and the fluorescence spectrum peak wavelength obtained by the fluorometer.

Further, the ultraviolet irradiation level control device may automatically change a control target value.

Furthermore, the fluorometer may monitor at least any one of the excitation spectrum peak wavelength in a range from 310 nm to 350 nm or fluorescence spectrum peak wavelengths in a range from 420 nm to 460 nm.

Moreover, the fluorometer may have, as an excitation light source, an LED which emits light of a wavelength from 310 nm to 350 nm.

A second aspect of the present invention provides a water quality monitoring instrument for monitoring quality of water to be monitored, the water quality monitoring instrument including fluorometer measuring an excitation spectrum peak wavelength of water to be treated and/or a fluorescence spectrum peak wavelength thereof; and a freshness calculation device calculating freshness of the water to be treated based on the excitation spectrum peak wavelength and/or the fluorescence spectrum peak wavelength obtained by the fluorometer.

In the water quality monitoring instrument according to the second aspect, the fluorometer may have, as an excitation light source, an LED which emits light of a wavelength from 310 nm to 350 nm.

According to the present invention, an optimum irradiation level can be secured even if the properties or conditions of the water to be treated are changed. Thus, reliability of the safety of ultraviolet-irradiated water and energy saving are achieved at the same time.

DESCRIPTION OF THE EMBODIMENTS

Description of Fluorescence Analysis

First, a description will be given of a fluorescence analysis used in an ultraviolet irradiation system and a water quality monitoring instrument according to the present invention prior to a detailed description of the ultraviolet irradiation system and the water quality monitoring instrument according to the present invention.

Fulvic acid-like organic compounds, also called humic matters, are contained in raw water of a river or the like and constitute a main body of a precursor of organohalogen compounds such as carcinogenic trihalomethane in chlorination of tap water. As to the fulvic acid-like organic compounds, it has been reported that there is a very high correlation between the concentration of the fulvic acid-like organic compounds in the water and the fluorescence intensity represented by an output value from a fluorometer.

Such a fluorescence analysis has the following features. The fluorescence analysis is so sensitive as to observe weak light emission from the fulvic acid-like organic compounds. Moreover, the fluorescence analysis has fewer errors attributable to turbidity than absorption spectrophotometry (E260) since light scattering is proportional to the wavelength to the fourth power. Furthermore, the fluorescence analysis enables continuous measurement using no reagent.

The absorption spectrophotometry (E260) that is an indicator of an organic matter concentration in the water is not suitable for measurement of ozonated water since ozone dissolved in the water also absorbs light. On the other hand, the fluorescence analysis is suitable for measurement of ozonated water since the ozonated water in the fluorescence analysis has no influence on measured values.

Figure 1:
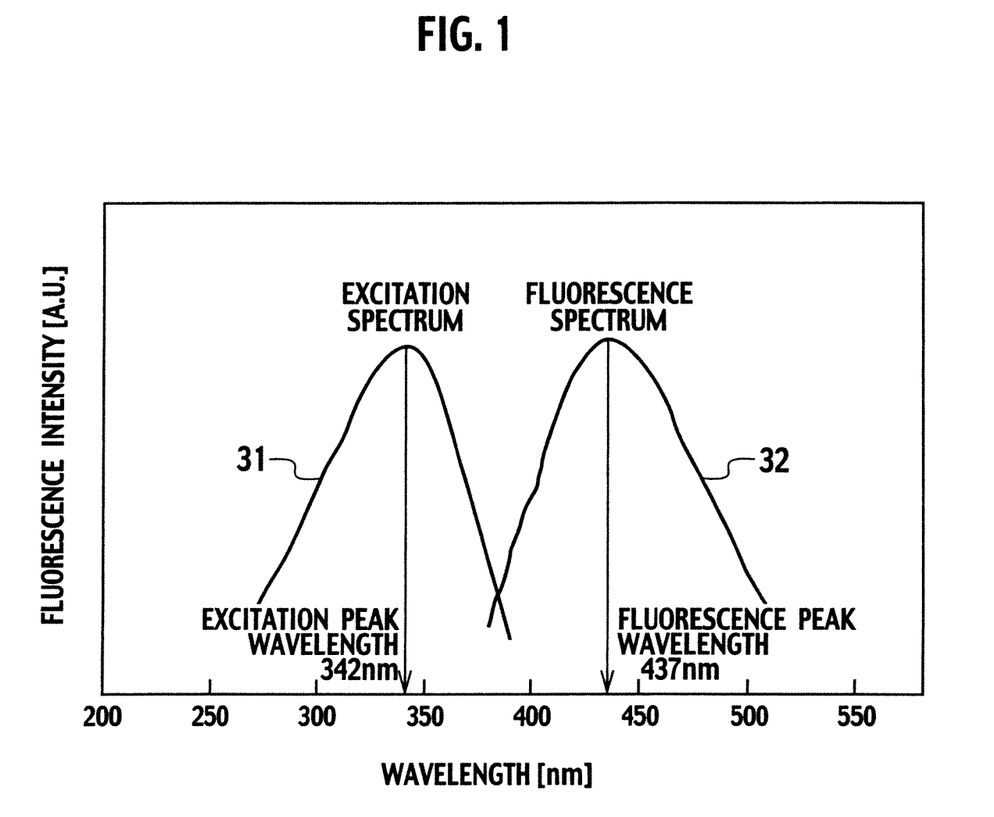
FIG. 1 shows an example of each of excitation and fluorescence spectra of a water sample taken from a downstream region of a river in a large city.

FIG. 1 shows an example of each of an excitation spectrum 31 and a fluorescence spectrum 32 of a water sample taken from a downstream region of a river in a large city. The excitation spectrum is a spectrum obtained by fixing a fluorescence wavelength to be observed to 425 nm and scanning an excitation wavelength from 270 nm to 390 nm. Meanwhile, the fluorescence spectrum is a spectrum obtained by fixing an excitation wavelength to 345 nm and scanning a fluorescence wavelength to be observed from 370 nm to 520 nm. The respective spectra have their peaks at 342 nm and 437 nm.

These spectra have the following characteristics. Specifically, the spectra are ideally mirror-symmetrical to each other and have different peak wavelengths depending on various environmental waters.

Figure 2:
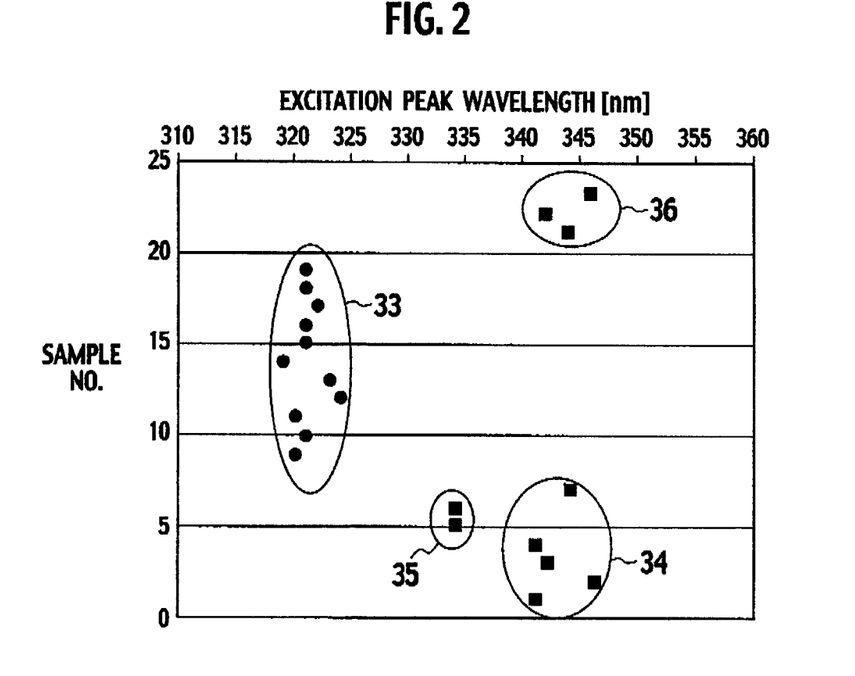
FIG. 2 shows an example of measurement of peak wavelengths of the excitation and fluorescence spectra for various environmental waters.

FIG. 2 shows an example of a result obtained by measuring peak wavelengths of the excitation and fluorescence spectra for various environmental waters. As to samples 33 taken from the uppermost water source region of the river, peak wavelengths of excitation spectra are concentrated around 320 nm. Meanwhile, as to samples 34 taken from the downstream region of the river, peak wavelengths are concentrated around 340 nm and 345 nm. Furthermore, samples 35 taken from a midstream region of the river represent wavelengths between the wavelengths represented by the both samples 33 and 34. As to samples 36 taken from secondary-treated sewage, peak wavelengths are concentrated around 345 nm. The above result shows that the peak wavelengths of the excitation spectra can be used for classification of the various environmental waters.

Figure 3:
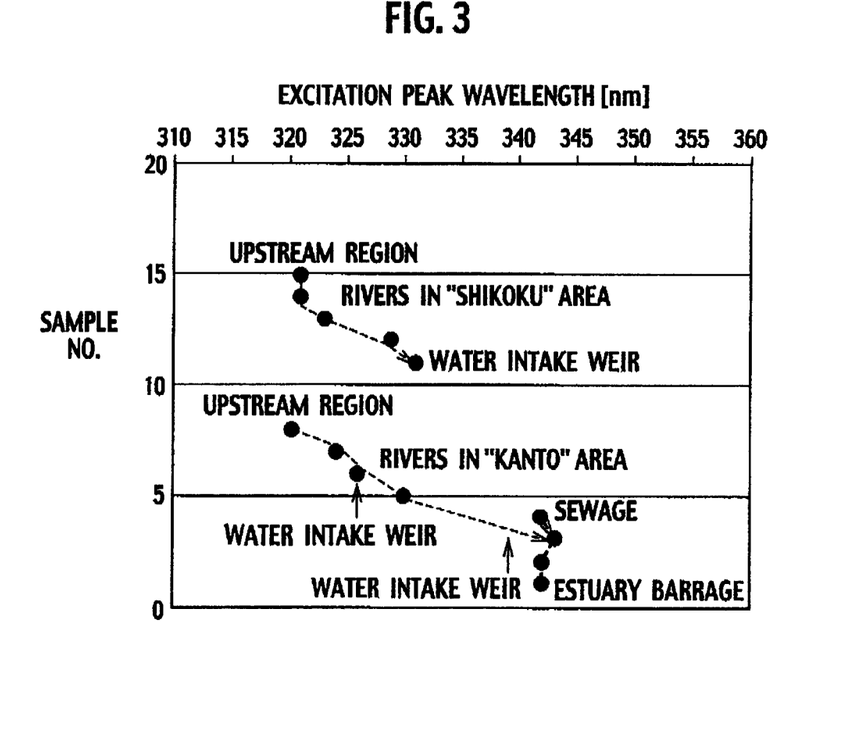
FIG. 3 shows an example of a result obtained by measuring excitation spectrum peak wavelengths of sample waters taken between upstream and downstream regions of representative rivers.

FIG. 3 shows an example of a result obtained by measuring peak wavelengths of excitation spectra of sample waters. These sample waters are taken between upstream and downstream regions of representative rivers. As shown in FIG. 3, it is evident how the peak wavelength of the excitation spectrum is shifted from a short wavelength to a long wavelength by mixing sewage into clear raw water.

The above results show the following. Specifically, the fluorescence intensity of the treated water to be measured is continuously observed by performing the fluorescence analyses while continuously leading the treated water to the fluorometer. Thus, the proportion of sewage mixed in the treated water can be continuously measured. More specifically, the intensity of fluorescence having a wavelength of 425 nm is continuously measured, which is emitted when the treated water that is continuously led is irradiated with excitation light having a predetermined wavelength, for example, a wavelength of 345 nm.

Accordingly, the continuous fluorescence analysis as described above contributes to securing high reliability of reduction in hygiene risks due to mixing of sewage for water purification processes in which securing water quality in terms of hygiene is the important target, and for industrial water and the like. Thus, it can provide an ultraviolet irradiation system, a water quality monitoring instrument and the like, which have the high reliability as described above. Moreover, it is possible to perform ultraviolet irradiation at an intensity commensurate with the proportion of sewage mixed in the treated water, as compared with conventional ultraviolet irradiation that is proportional to a volume of water or performed at a certain intensity, and also to control the ultraviolet irradiation. Therefore, it is possible to make an ultraviolet disinfection equipment which can achieve both energy saving and reliability of the safety.

Figure 4:
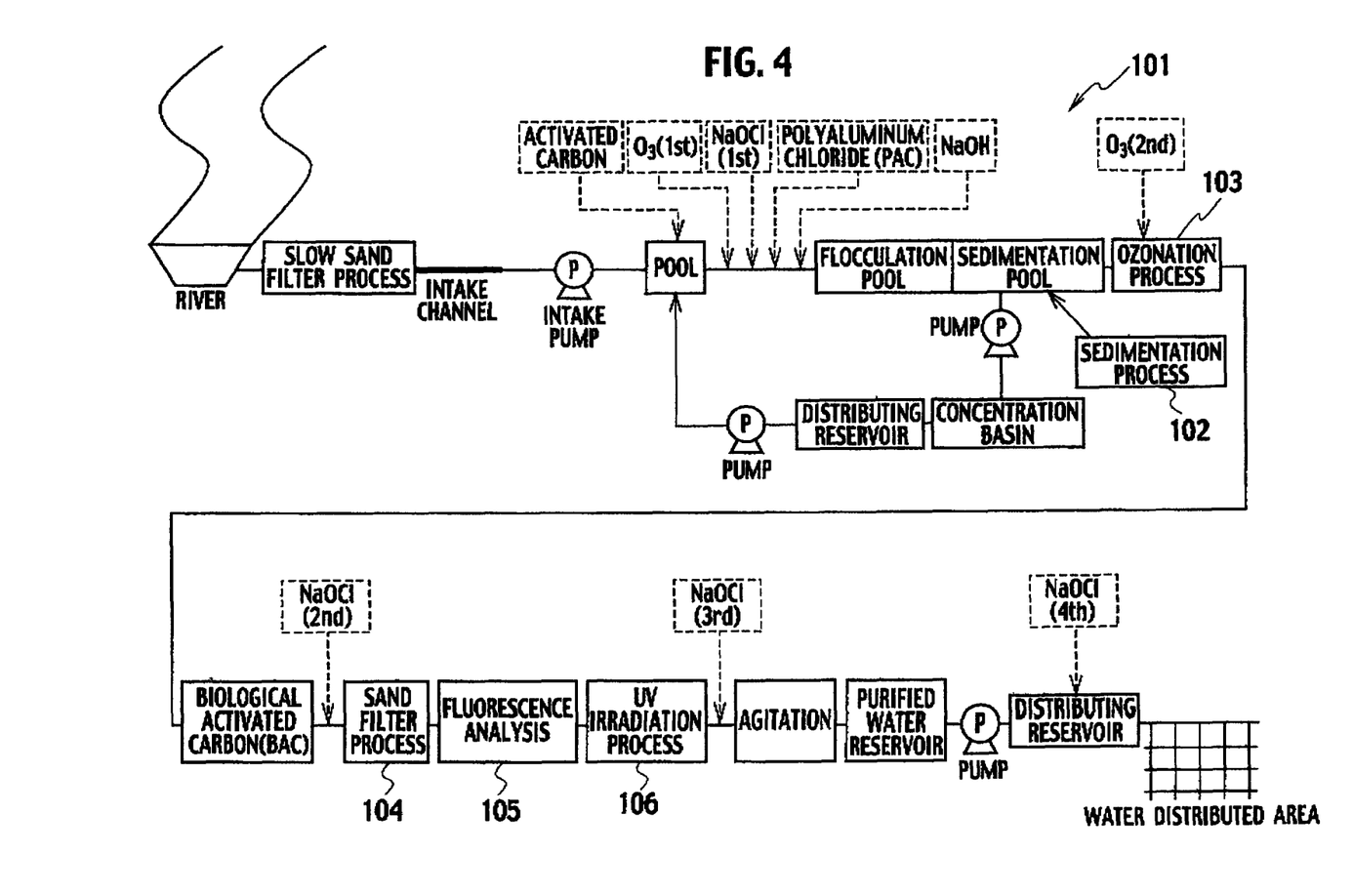
FIG. 4 is a block diagram showing an example of a treatment process at a general water purification plant.

FIG. 4 shows an example of applying the ultraviolet irradiation and the fluorescence analysis described above to a water purification plant 101. In this case, it is particularly effective to irradiate highly treated water with ultraviolet rays, the highly treated water being obtained after removal of turbidity in a sedimentation process 102 and the like or after an ozonation process 103. Therefore, a fluorescence analysis 105 is performed after a sand filtration process 104 following the sedimentation process 102 and the ozonation process 103. Thereafter, an ultraviolet irradiation process 106 of irradiating the water with ultraviolet rays is executed based on a result of the fluorescence analysis. Subsequently, a residual chlorine agent is further added to the water having been disinfected by the ultraviolet irradiation.

Next, a description of the ultraviolet irradiation system and the water quality monitoring instrument according to the present invention will be given with showing following embodiments.

Note that, in the following embodiments, a description will be given of the case where the present invention is applied to a water purification plant and the like, which put hygienic importance on securing water quality. However, the present invention can also be applied to various plants and the like, which require securing reliability of reduction in hygiene risks due to mixing of sewage, such as the field of industrial water treatment which similarly requires securing water quality.

First Embodiment

Figure 5:
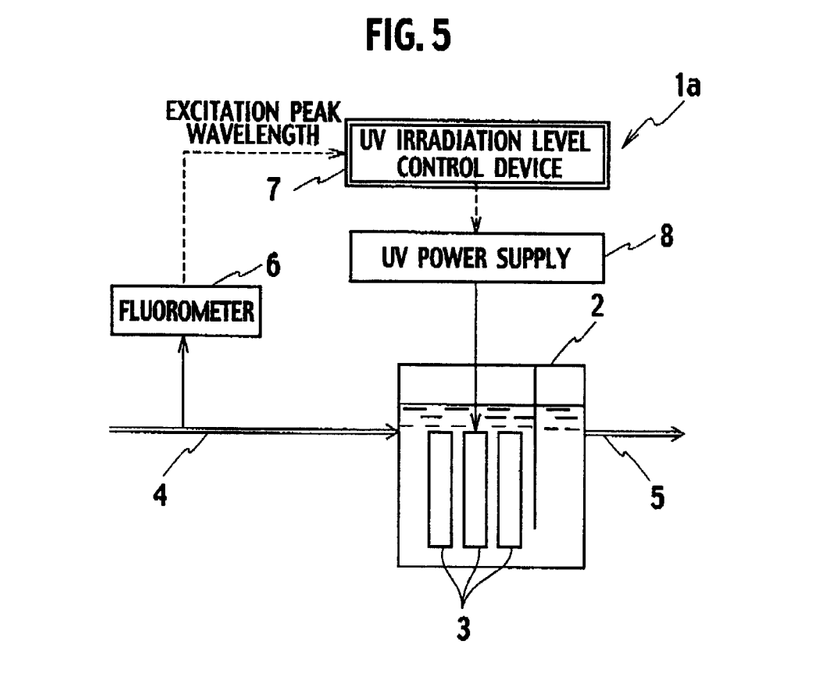
FIG. 5 is a configuration diagram schematically showing first and second embodiments of an ultraviolet irradiation system according to the present invention.

FIG. 5 is a configuration diagram schematically showing a first embodiment of an ultraviolet irradiation system according to the present invention.

As shown in FIG. 5, an ultraviolet irradiation system 1a includes an ultraviolet irradiation tank 2, an ultraviolet irradiation device 3, a fluorometer 6, an ultraviolet (UV) irradiation level control device 7 and an ultraviolet (UV) power supply 8. The ultraviolet irradiation tank 2 continuously takes in pre-treated water 4. Here, the pre-treated water 4 refers to water in a state after water purification, such as a sand filtration process and a high treatment process, has been performed on river raw water taken in and before a third injection of chloride is carried out (see FIG. 4). The ultraviolet irradiation device 3 is provided in the ultraviolet irradiation tank 2, generates ultraviolet rays having an intensity corresponding to a driving voltage supplied from the ultraviolet power supply 8 (to be described later) and irradiates the pre-treated water 4 in the ultraviolet irradiation tank 2 with the ultraviolet rays. Thereafter, the pre-treated water 4 irradiated with the ultraviolet rays is discharged as ultraviolet-irradiated water 5 from the ultraviolet irradiation tank 2. The fluorometer 6 includes an excitation light source such as a mercury lamp or an LED. The fluorometer 6 continuously takes in a part of the pre-treated water 4 flowing into the ultraviolet irradiation tank 2. At the same time, the fluorometer 6 fixes a fluorescence wavelength to be observed to 425 nm and scans an excitation wavelength to obtain an excitation spectrum of the pre-treated water 4. Thus, the fluorometer 6 continuously measures the excitation peak wavelength of the pre-treated water 4. The ultraviolet irradiation level control device 7 uses an analysis result (the excitation peak wavelength) obtained by the fluorometer 6 to calculate an ultraviolet irradiation level target value for optimizing an ultraviolet irradiation level. The ultraviolet power supply 8 generates a driving voltage corresponding to the ultraviolet irradiation level target value outputted from the ultraviolet irradiation level control device 7 and supplies the driving voltage to the ultraviolet irradiation device 3.

With the above configuration, the irradiation level of the ultraviolet rays emitted from the ultraviolet irradiation device 3 is optimized. In other words, the pre-treated water 4 is irradiated with just enough ultraviolet rays.

Figure 6:
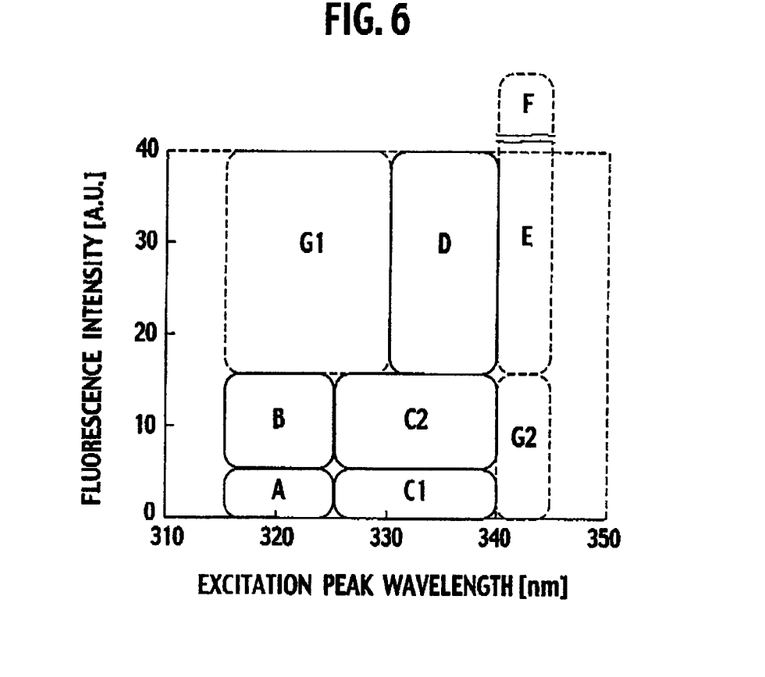
FIG. 6 shows an example of broad classification of environmental waters by use of a water quality matrix representing a correlation between an excitation peak wavelength and a fluorescence intensity, which are measured by a fluorometer in the first embodiment.

FIG. 6 shows an example of broad classification of environmental waters (the pre-treated waters 4) by a water quality matrix representing a correlation between the excitation peak wavelength (the peak wavelength of the excitation spectrum) measured by the fluorometer 6 and a fluorescence intensity.

The environmental water classified in a region A is clear raw water. FIG. 6 shows that the clear raw water has a short excitation peak wavelength and a fluorescence intensity of 5 or less. Similarly, the environmental water in a region B is water obtained by subjecting relatively clear raw water to sand filtration. The environmental water in a region C1 is highly treated water obtained by treating surface raw water of a river in a large city. The environmental water in a region C2 is water obtained by subjecting the surface raw water of the river in the large city to conventional sand filtration. The environmental water in a region D is surface water taken from a midstream region of the river in the large city. The environmental water in a region E is surface water taken from a downstream region of the river in the large city. The environmental water in a region F is secondary-treated sewage. The environmental water in a region G1 is water in a monitoring region indicating a possibility of mixing of a fluorescent material other than those caused by sewage. The environmental water in a region G2 is water, although having a low level of "freshness" (to be described later), obtained by subjecting fulvic acid-like organic compounds to oxidation treatment by performing some kind of high treatment. In other words, the environmental water in the region G2 is water belonging to a hygienically high-risk region indicating water that is frequently recycled, and the like.

Moreover, although the secondary-treated sewage in the region F is classified in a narrow region from 340 nm to 345 nm, this is a particular case where the fluorescence intensity (relative) is between several hundred and two thousand and several hundred. When the secondary-treated sewage is released to the river and mixed with clear environmental water, the fluorescence intensity of the mixed water in the downstream region of the river becomes about several tens because the secondary-treated sewage is well diluted in the river. However, water containing the secondary-treated sewage has a characteristic that the excitation peak wavelengths are concentrated in a limited range of longer wavelengths as described above.

Figure 7:
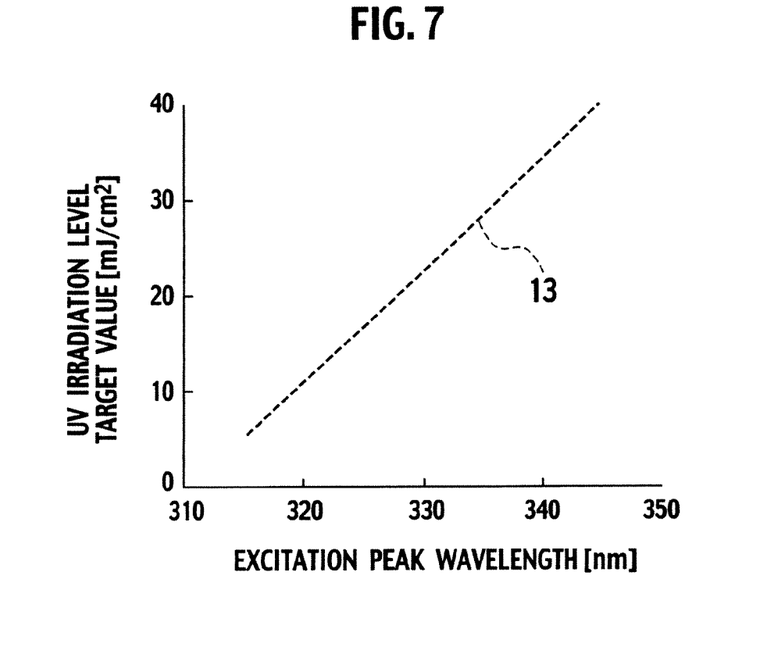
FIG. 7 is a graph showing an example of a relationship between the excitation peak wavelength measured by the fluorometer in the first embodiment and an ultraviolet irradiation level target value.

FIG. 7 shows an example of a graph representing a relationship between the excitation peak wavelength measured by the fluorometer 6 and the ultraviolet irradiation level target value. As is clear from this example, the ultraviolet irradiation level target value is increased with an increase in the excitation peak wavelength, as shown by a proportional function 13. Therefore, the ultraviolet irradiation level target value is proportionally-controlled based on the excitation peak wavelength.

As to the ultraviolet irradiation level required for the inactivation of chlorine-resistant pathogenic microorganisms, for example, in the proceedings on the 51st seminar of Japan Society on Water Environment, January 2006, it is shown that an effect of such an inactivation appears at 5 mJ/cm$^2$ and the inactivation can be surely completed at 40 mJ/cm$^2$. Therefore, the environmental waters from the clear raw water having the excitation peak wavelength of 316 nm up to the water taken from the downstream region of the river or the secondary-treated sewage having the excitation peak wavelength of 345 nm are irradiated with the ultraviolet rays at the irradiation levels proportional to the respective wavelengths.

Thus, while the conventional ultraviolet irradiation is performed at a fixed irradiation level (that is 40 mJ/cm$^2$), control of the ultraviolet irradiation level appropriate for the water quality of the pre-treated water 4 can be achieved according to this embodiment. Consequently, an energy saving effect is expected.

As described above, in the first embodiment, a part of the pre-treated water 4 flowing into the ultraviolet irradiation tank 2 is guided to the fluorometer 6, and measured to obtain an excitation spectrum of the pre-treated water 4 in the state where the fluorescence wavelength is fixed to 425 nm, and therefore the excitation peak wavelength is continuously measured. At the same time, the analysis result obtained by the fluorometer 6 is used to calculate the ultraviolet irradiation level target value required for optimizing the ultraviolet irradiation level. Moreover, the irradiation level of the ultraviolet rays emitted from the ultraviolet irradiation device 3 is controlled. Therefore, even if the water quality of the pre-treated water 4 is changed, the ultraviolet irradiation level is automatically optimized. Thus, improvement in the safety of the ultraviolet-irradiated water 5 and the energy saving can be achieved at the same time.

Moreover, in the first embodiment, the fluorescence analysis of the pre-treated water 4 is performed by using the range of wavelengths from 310 nm to 350 nm as the peak wavelength of the excitation spectrum and the range of wavelengths from 420 nm to 460 nm as the peak wavelength of the fluorescence spectrum. Thus, the water quality of the pre-treated water 4 can be accurately measured. Moreover, reliability of the safety of the ultraviolet-irradiated water 5 and the energy saving can be achieved at the same time by optimizing the ultraviolet irradiation level.

Furthermore, in the first embodiment, an LED that emits an ultraviolet light of a wavelength about 310 nm may be used as a light source of the fluorometer 6. Thus, in this case, there can be no need to be concerned about instability of lamp illuminance unlike the case of the mercury lamp or the like, which has heretofore been widely used. Moreover, periodical (for example, once a year) part replacement or the like is no longer required. Thus, the effort and cost of maintenance and management can be reduced.

Second Embodiment

Next, a description will be given of a second embodiment of the ultraviolet irradiation system according to the present invention. Note that, since a system configuration is the same as that of the first embodiment shown in FIG. 5, a description will be given by using FIG. 5 without modification.

The ultraviolet irradiation level control device 7 in the first embodiment sets the excitation peak wavelength and the ultraviolet irradiation level target value so as to have a linearly proportional relationship. In other words, the ultraviolet irradiation level target value in the first embodiment is a linear function of the excitation peak wavelength. Meanwhile, an ultraviolet irradiation level control device 7 in the second embodiment sets an ultraviolet irradiation level target value to be a step function of an excitation peak wavelength. Specifically, hygienic reliability and energy saving are further improved by setting the ultraviolet irradiation level target value to be increased in stages as the excitation peak wavelength is increased.

Figure 8:
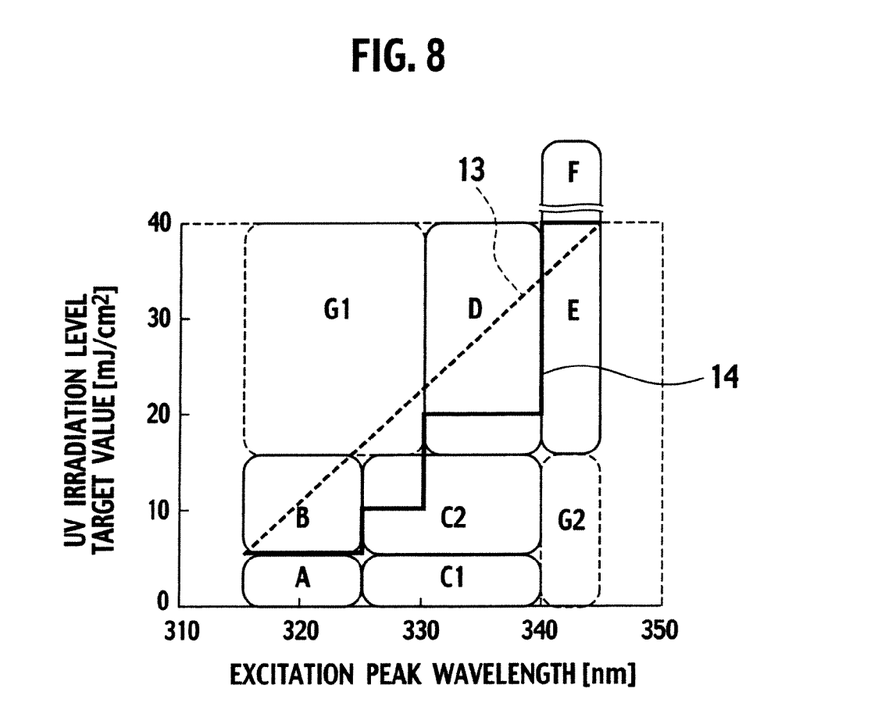
FIG. 8 shows an example of a relationship between a water quality matrix representing a correlation between an excitation spectrum peak wavelength and a fluorescence intensity, which are obtained by a fluorometer in the second embodiment, and an ultraviolet irradiation level target value outputted from an ultraviolet irradiation level control device.

FIG. 8 shows an example of the ultraviolet irradiation level target value corrected based on the water quality matrix representing the correlation between the peak wavelength of the excitation spectrum and the fluorescence intensity. As shown in this figure, the ultraviolet irradiation level target value follows a step function 14 that is changed in stages as the peak wavelength of the excitation spectrum is increased.

In the region A, the ultraviolet irradiation level target value is minimum and constant at 5 mJ/cm$^2$. In a part of the regions C1 and C2, the ultraviolet irradiation level target value is constant at 10 mJ/cm$^2$. However, the ultraviolet irradiation level target value is set constant at 20 mJ/cm$^2$ from the excitation peak wavelength of 330 nm and above where the region D appears. Furthermore, the ultraviolet irradiation level target value is set maximum and constant at 40 mJ/cm$^2$ from the excitation peak wavelength of 340 nm and above where the hygienically high-risk region E appears.

As described above, by setting the ultraviolet irradiation level target value in stages according to the peak wavelength of the excitation spectrum, the ultraviolet irradiation level target value more appropriate for the water quality can be automatically set compared with the linearly proportional ultraviolet irradiation level target value indicated by the dotted line in FIG. 8. Therefore, both of the hygienic reliability and the energy saving can be achieved.

Moreover, needless to say, a peak wavelength of a fluorescence spectrum, which is ideally mirror-symmetrical to the peak wavelength of the excitation spectrum, can be used instead for determination of the ultraviolet irradiation level target value described above.

Third Embodiment

Figure 9:
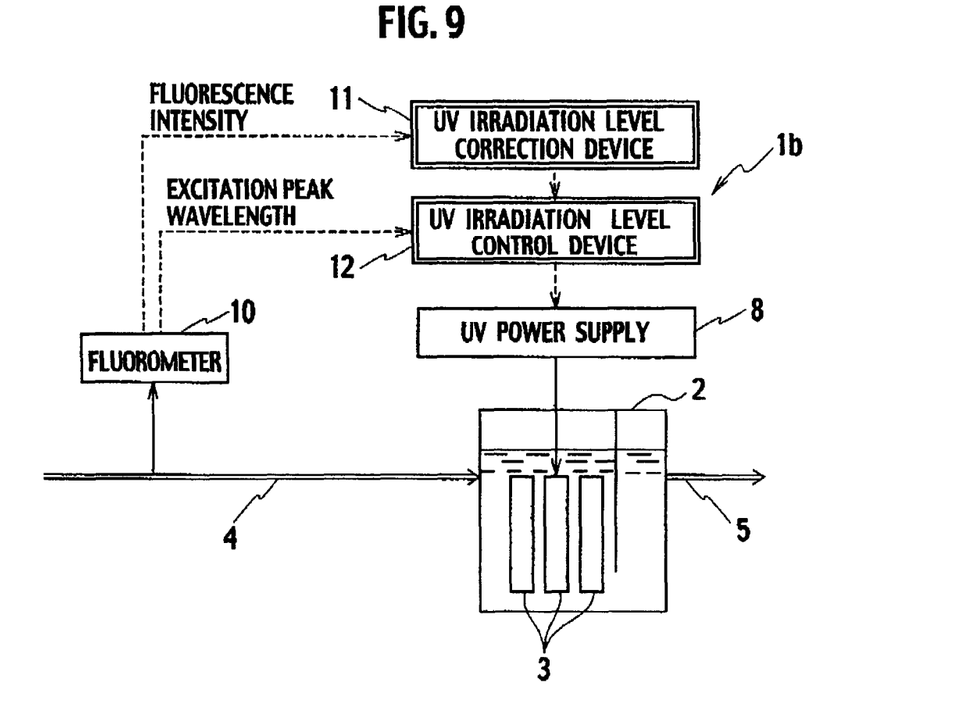
FIG. 9 is a configuration diagram schematically showing a third embodiment of the ultraviolet irradiation system according to the present invention.

FIG. 9 is a configuration diagram schematically showing a third embodiment of the ultraviolet irradiation system according to the present invention. Note that parts corresponding to the parts shown in FIG. 5 are denoted by the same reference numerals in FIG. 9.

As shown in FIG. 9, an ultraviolet irradiation system 1b in the third embodiment is different from the ultraviolet irradiation system 1a in the first and second embodiments shown in FIG. 5 in the following points. Specifically, 1) a fluorometer 10 fixes a fluorescence wavelength to 425 nm, scans an excitation wavelength to obtain an excitation spectrum of pre-treated water 4 and continuously measure both a fluorescence intensity and an excitation peak wavelength. Moreover, 2) there is provided an ultraviolet irradiation level control device 12 which shifts an ultraviolet irradiation level target value in stages according to the excitation peak wavelength and a correction coefficient. Further, 3) there is provided an ultraviolet irradiation level correction device 11 which calculates an ultraviolet irradiation level correction value by use of the fluorescence intensity obtained by the fluorometer 10. Furthermore, 4) an excitation peak wavelength and a fluorescence intensity are simultaneously measured for the pre-treated water 4. Thereafter, the correction coefficient is calculated by taking into consideration the fluorescence intensity. Thus, an ultraviolet irradiation level target value calculated by the ultraviolet irradiation level control device 12 is corrected.

Figure 10:
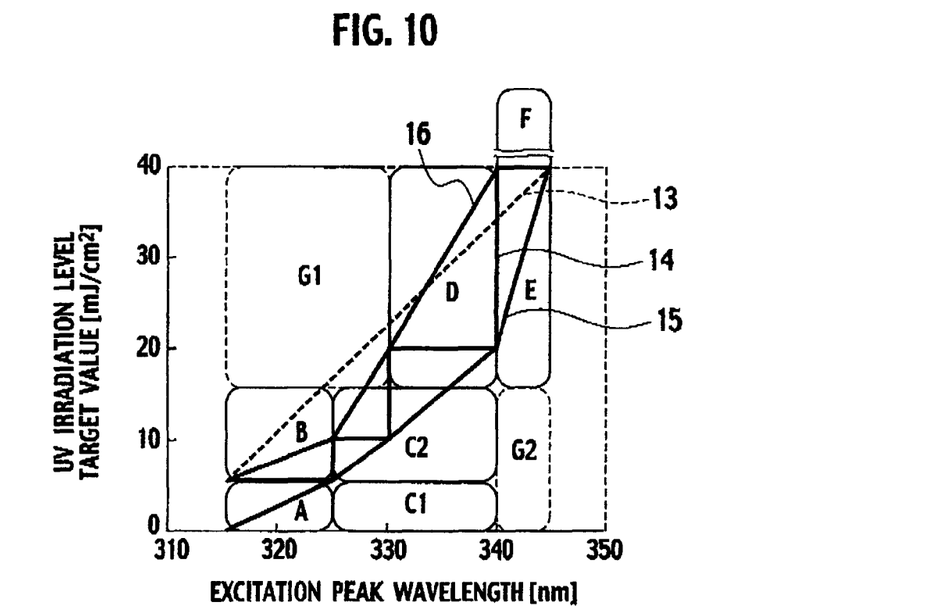
FIG. 10 shows an example of an ultraviolet irradiation level target value corrected by use of continuously measured fluorescence intensity from an ultraviolet irradiation level target value that is corrected in a step-like manner based on a water quality matrix representing a correlation between an excitation spectrum peak wavelength and a fluorescence intensity, which are obtained by a fluorometer in the third embodiment.

FIG. 10 is an explanatory view showing an example of an ultraviolet irradiation level target value according to the third embodiment, which is corrected by continuously measured fluorescence intensity based on an ultraviolet irradiation level target value that is changed in a step-like manner in the water quality matrix representing the correlation between the peak wavelength of the excitation spectrum and the fluorescence intensity. This figure also shows the proportional function 13 described in the first embodiment by the dotted line and the step function 14 described in the second embodiment, as a reference.

Among samples (pre-treated water 4) in each region of the water quality matrix, one sample showing higher fluorescence intensity than others represents that the one contains more fulvic acid-like organic compounds than others. Thus, it can be said that the one is more significantly influenced by daily life and industrial activities. Therefore, in order to perform ultraviolet irradiation most suitable for such a sample, a correction coefficient corresponding to the fluorescence intensity is obtained to correct the ultraviolet irradiation level target value. The ultraviolet irradiation level target value corrected with the correction coefficient is set within a range surrounded by a "minimum target value pattern" 15 and a "maximum target value pattern" 16. Here, the "minimum target value pattern" 15 is expressed by a line connecting points corresponding to the longest excitation peak wavelengths among the excitation peak wavelengths at the same ultraviolet irradiation level target value in the step function 14 as shown in FIG. 10, for example. Moreover, the "maximum target value pattern" 16 is similarly expressed by a line connecting points corresponding to the shortest excitation peak wavelengths among the excitation peak wavelengths at the same ultraviolet irradiation level target value in the step function 14.

In the ultraviolet irradiation based on the maximum target value pattern 16, a higher level of energy saving can be achieved compared with the ultraviolet irradiation level target value expressed by the proportional function 13 shown in FIG. 7. Moreover, in the hygienically high-risk regions D and E, the ultraviolet irradiation level can be operated toward the safe side. Also in the ultraviolet irradiation based on the minimum target value pattern 15, a significantly higher level of energy saving can be achieved compared with the ultraviolet irradiation level target value expressed by the proportional function 13.

Thus, in the third embodiment, the ultraviolet irradiation level target value more appropriate for the water quality than the ultraviolet irradiation level target value expressed by the proportional function 13 can be automatically set in each of the regions as in the case of the second embodiment. Therefore, both of the hygienic reliability and the energy saving can be achieved. Note that the ultraviolet irradiation level control pattern is more smoothly continuous compared with the stepwise pattern of the ultraviolet irradiation level target value. Thus, excellent controllability is achieved.

Moreover, needless to say, a peak wavelength of a fluorescence spectrum, which is ideally mirror-symmetrical to the peak wavelength of the excitation spectrum, can be used instead for determination of the ultraviolet irradiation level target value described above.

Fourth Embodiment

Figure 11:
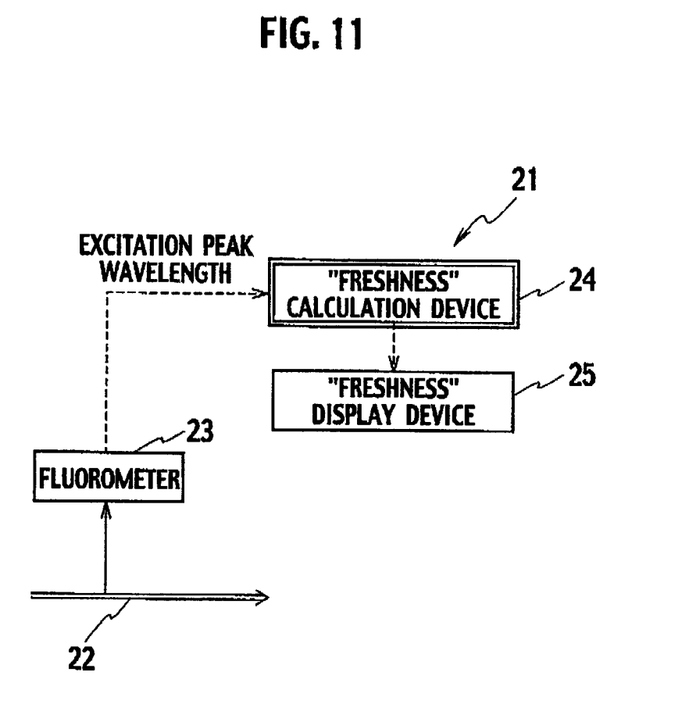
FIG. 11 is a configuration diagram schematically showing a water quality monitoring instrument according to fourth and fifth embodiments of the present invention.

A water quality monitoring instrument according to a fourth embodiment of the present invention will be described. FIG. 11 is a configuration diagram schematically showing the water quality monitoring instrument of the present embodiment.

A water quality monitoring instrument 21 shown in FIG. 11 includes a fluorometer 23, a "freshness" calculation device 24 and a "freshness" display device 25. Here, the "freshness" is an index indicating the degree of utilization of the river water as described later. While continuously taking in river water (sample water) 22 from a river to be monitored (a monitoring target river), the fluorometer 23 fixes a fluorescence wavelength to 426 nm and scans an excitation wavelength to obtain an excitation spectrum of the sample water. Thus, the fluorometer 23 continuously measures the excitation peak wavelength. The "freshness" calculation device 24 uses an analysis result obtained by the fluorometer 23 to calculate "freshness" indicating a degree of utilization of the river water 22. The "freshness" display device 25 has a large electronic signboard or the like which is placed at a river area or the like, and displays the "freshness" obtained by the "freshness" calculation device 24. With the above configuration, the water quality monitoring instrument 21 performs a fluorescence analysis by taking the river water 22 from the monitoring target river, calculates "freshness" by use of an excitation peak wavelength obtained by the fluorescence analysis, and displays the "freshness" on the large electronic signboard or the like.

Thus, the "freshness" can be recognized just by looking at the large electronic signboard or the like.

The "freshness" is one of new indices about rivers, which are established by the Ministry of Land, Infrastructure and Transport and the like and indicates the degree of utilization of the river water. The establishment of the index is based on the following background. Specifically, a rate of norovirus disease prevalence from tap water, which is caused by circulation of sewage and purified raw water in a large city area, starts to be increased. Thus, public awareness of such problems is growing.

The "freshness" is calculated by the following equation,

"Freshness"=(1−amount of water used at calculation point/river flow rate)×100%.

This equation shows that the higher the "freshness", the smaller the proportions of living drainage, drainage from sewage treatment plants and the like, factory drainage and drainage from livestock farms to the amount of water flowing through a calculation point. Particularly, rivers in "Kanto" and "Kinki" areas, in which urbanization has advanced, tend to have lower indices.

As described above, in the fourth embodiment, the fluorescence analysis is performed by taking the river water 22 from the monitoring target river, the "freshness" is calculated by use of the excitation peak wavelength obtained by the fluorescence analysis, and the "freshness" is displayed on the large electronic signboard or the like. Therefore, it is possible to let people around the river know the water quality by measuring and displaying the "freshness" of the monitoring target river.

Fifth Embodiment

Next, a water quality monitoring instrument according to a fifth embodiment of the present invention will be described. Note that, since a system configuration is the same as that of the fourth embodiment shown in FIG. 11, a description will be given by using FIG. 11.

A water quality monitoring instrument 21 according to the fifth embodiment includes a fluorometer 23, a "freshness" calculation device 24 and a "freshness" display device 25. The fluorometer 23 includes an excitation light source having an LED which emits light of a wavelength from 310 nm to 350 nm. While taking in river water 22 from a river to be monitored, the fluorometer 23 fixes a fluorescence wavelength to "425 nm" and scans an excitation wavelength to obtain an excitation spectrum of the sample water. Thus, the fluorometer 23 measures an excitation peak wavelength of the river water 22. The "freshness" calculation device 24 is formed of a semiconductor element and the like, and uses an analysis result obtained by the fluorometer 23 to calculate "freshness" indicating a degree of utilization of the river water 22. The "freshness" display device 25 is formed of a liquid crystal display device or the like, and displays the "freshness" obtained by the "freshness" calculation device 24. The water quality monitoring instrument 21 is carried by a river administrator or the like. When the river water 22 taken from the monitoring target river is set in the fluorometer 23 and an analysis start switch is operated, the water quality monitoring instrument 21 measures an excitation peak wavelength by performing a fluorescence analysis and calculates "freshness" by use of the excitation peak wavelength. This "freshness" is displayed on the "freshness" display device 25.

As described above, in the fifth embodiment, the water quality monitoring instrument 21 is reduced in size so as to be portable. Therefore, the "freshness" can be quickly obtained by sending the manager of the river or the like to the river to be monitored.

What is claimed is:

1. An ultraviolet irradiation system for disinfecting water with ultraviolet rays, comprising:
   an ultraviolet irradiation tank;
   a pre-treated water input line configured to provide pre-treated water to the ultraviolet irradiation tank, the pre-treated water having undergone an initial ozonation process and a final ozonation process;
   a fluorometer disposed in at least one point in a process before a disinfection process and after the final ozonation process, the fluorometer configured to continuously measure a fluorescence intensity of the pre-treated water and at least one of an excitation spectrum peak wavelength and a fluorescence spectrum peak wavelength of the pre-treated water;
   an ultraviolet irradiation level correction device configured to calculate an ultraviolet irradiation level correction value from the fluorescence intensity obtained by the fluorometer;
   an ultraviolet irradiation level control device configured to calculate an ultraviolet irradiation level of the ultraviolet rays from a step function thereof in a water quality matrix according to at least one of the excitation spectrum peak wavelength and the fluorescence spectrum peak wavelength obtained by the fluorometer, the water quality matrix representing a correlation between the fluorescence intensity of the pre-treated water and any one of the excitation spectrum peak wavelength and the fluorescence spectrum peak wavelength of the pre-treated water, the water quality matrix including regions classified by the correlation, the step function being defined by the regions of the water quality matrix, and the ultraviolet irradiation level control device configured to calculate a target value for optimizing the ultraviolet irradiation level of the ultraviolet rays in the disinfection process by a correction of the calculated ultraviolet irradiation level with the ultraviolet irradiation level correction value calculated by the ultraviolet irradiation level correction device;
   an ultraviolet irradiation device provided in the ultraviolet irradiation tank; and
   an ultraviolet power supply configured to generate a driving voltage corresponding to the ultraviolet irradiation level target value and supply the driving voltage to the ultraviolet irradiation device;
   wherein the ultraviolet irradiation device is configured to generate the ultraviolet rays having an intensity corresponding to the driving voltage and irradiate the pre-treated water in the ultraviolet irradiation tank with the generated ultraviolet rays; and
   wherein the ultraviolet irradiation level correction value is set to a value to set the target value within a range surrounded by a first pattern and a second pattern, the first pattern is defined by lines connecting points corresponding to the longest excitation spectrum peak wavelengths or fluorescence spectrum peak wavelength at stages of the step function, and the second pattern is defined by lines connecting points corresponding to the shortest excitation spectrum peak wavelengths or fluorescence spectrum peak wavelength at the stages of the step function.

2. The ultraviolet irradiation system according to claim 1, wherein the ultraviolet irradiation level control device automatically changes the target value.

3. The ultraviolet irradiation system according to claim 1, wherein the fluorometer monitors at least any one of the excitation spectrum peak wavelength in a range from 310 nm to 350 nm and the fluorescence spectrum peak wavelength in a range from 420 nm to 460 nm.

4. The ultraviolet irradiation system according to claim 1, wherein the fluorometer has, as an excitation light source, an LED that emits light of a wavelength from 310 nm to 350 nm.

* * * * *